United States Patent
Jin

(10) Patent No.: US 9,658,200 B2
(45) Date of Patent: May 23, 2017

(54) CONTROL METHOD OF SENSOR DISPOSED IN EXHAUST SYSTEM

(71) Applicants: Hyundai Motor Company, Seoul (KR); Kia Motors Corporation, Seoul (KR)

(72) Inventor: Jeong Sik Jin, Ansan-si (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 689 days.

(21) Appl. No.: 14/143,461

(22) Filed: Dec. 30, 2013

(65) Prior Publication Data

US 2014/0358467 A1 Dec. 4, 2014

(30) Foreign Application Priority Data

Jun. 3, 2013 (KR) ........................ 10-2013-0063708

(51) Int. Cl.
| | | |
|---|---|---|
| *G01B 5/18* | (2006.01) | |
| *G01B 7/26* | (2006.01) | |
| *G01B 11/22* | (2006.01) | |
| *G01B 13/14* | (2006.01) | |
| *G01B 21/18* | (2006.01) | |
| *G01N 33/00* | (2006.01) | |
| *G01N 27/406* | (2006.01) | |

(52) U.S. Cl.
CPC ..... *G01N 33/0075* (2013.01); *G01N 27/4067* (2013.01)

(58) Field of Classification Search
CPC ......... Y02T 10/47; Y02T 10/26; Y02T 10/42; Y02T 10/44; Y02T 10/46; Y02T 10/144; Y02T 10/24; Y02T 10/40; Y02T 10/18; Y02T 10/36; Y02T 10/16; Y02T 10/166; Y02T 10/12; Y02T 10/121; Y02T 10/128
See application file for complete search history.

(56) References Cited

U.S. PATENT DOCUMENTS

| | | | | |
|---|---|---|---|---|
| 7,555,895 | B2 * | 7/2009 | Shirakawa | ............ F01N 3/0842 60/274 |
| 2007/0271904 | A1 * | 11/2007 | Shouda | ................... F01N 9/005 60/284 |

FOREIGN PATENT DOCUMENTS

JP 8-232746 A 9/1996

* cited by examiner

*Primary Examiner* — Roy Y Yi
(74) *Attorney, Agent, or Firm* — Morgan Lewis & Bockius LLP

(57) ABSTRACT

A control method of a sensor disposed in an exhaust system may include starting an engine; performing a first logic of checking whether moisture formed on a first sensor detecting one of the characteristics of exhaust gases emitted from the engine; when it is determined by the first logic that the moisture formed on the first sensor has evaporated, heating the first sensor; and performing a second logic of checking whether moisture formed on a second sensor disposed at the rear of the first sensor and detecting one of the characteristics of the exhaust gases.

11 Claims, 9 Drawing Sheets

CONTROL METHOD OF SENSOR DISPOSED IN EXHAUST SYSTEM

CROSS-REFERENCE TO RELATED APPLICATION

The present application claims priority to Korean Patent Application No. 10-2013-0063708 filed on Jun. 3, 2013, the entire contents of which is incorporated herein for all purposes by this reference.

BACKGROUND OF THE INVENTION

Field of the Invention

The present invention relates to a control method of a sensor disposed in an exhaust system, by which moisture formed on sensors disposed in an exhaust line is evaporated and the sensors are then heated to improve the durability of the sensors and prevent malfunctioning.

Description of Related Art

In general, an exhaust line is equipped with sensors (Lambda sensors, nitrogen oxide sensors, PM sensors, or temperature sensors) that are required to be heated by sensor heaters.

These sensors should be heated after evaporating all moisture, such as condensed water, to protect related parts. That is, when power is applied to the sensor heaters before moisture evaporates, an electric shock (short circuit) may damage peripheral parts due to the generation of high current/high-temperature heat.

In reality, if the engine stops working, the exhaust line is cooled to produce condensed water, and this condensed water is formed in the form of moisture on each sensor. When the engine is started and the temperature of exhaust gases rises, the moisture formed on each sensor evaporates.

When power is applied to the sensor heaters that heat the sensors, with moisture present on each sensor, this may deteriorate the durability of the sensors and cause the sensors to operate abnormally, as described above.

As a related conventional technology, Patent NO. 2995-051554 was disclosed which relates to an apparatus and method for preheating an oxygen sensor.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a control method of a sensor disposed in an exhaust system, which makes it easy to check the evaporation of moisture formed on sensors disposed in an exhaust line, and applies power to a sensor heater if it is determined that all the moisture is considered to have evaporated, thereby improving the durability of the sensors and preventing malfunctioning.

In an aspect of the present invention, a control method of a sensor disposed in an exhaust system, may include starting an engine, performing a first logic of checking whether moisture formed on a first sensor detecting one of characteristics of exhaust gases emitted from the engine, heating the first sensor when it is determined by the first logic that the moisture formed on the first sensor may have evaporated, and performing a second logic of checking whether moisture formed on a second sensor disposed at a rear of the first sensor and detecting one of the characteristics of the exhaust gases.

The control method may include heating the second sensor, when it is determined by the second logic that the moisture formed on the second sensor may have evaporated, and sequentially checking evaporation of moisture formed on other sensors disposed at a rear of the second sensor and each detecting one of the characteristics of the exhaust gases.

The first logic may include checking whether the first sensor detecting a temperature of the exhaust gases is out of order, determining whether an RPM of the exhaust gases is within a set value range, determining whether the temperature of the exhaust gases detected by the first sensor is higher than a set value, and determining that the moisture formed on the first sensor may have evaporated, when the first sensor is not out of order, the RPM of the engine is within the set value range, and the temperature of the exhaust gases is higher than the set value.

The control method may further may include determining whether the temperature of the exhaust gases detected by the first sensor is maintained for a predetermined time period.

The first logic may include checking whether the first sensor is out of order or not present, determining whether an RPM of the engine is within a set value range, determining whether a cumulative amount of fuel injection after a startup of the engine is greater than a set value, determining whether a set time may have elapsed after the startup of the engine, and determining that the moisture formed on the first sensor may have evaporated, when the first sensor is out of order or not present, the RPM of the engine is within the set value range, the cumulative amount of fuel injection is greater than the set value, and the set time may have elapsed.

The first logic may include supplying power to a first sensor heater for heating the first sensor during a second set time in a first set time cycle, determining whether a current consumed by the first sensor is between set lower and upper limit values, supplying power to the first sensor heater of the first sensor during the second set time in a third set time cycle shorter than the first set time cycle, determining again whether the current consumed by the first sensor is between the set lower and upper limit values, and determining whether the moisture formed on the first sensor may have evaporated, when the current consumed while supplying the power during the second set time in the first set time cycle is between the set lower and upper limits, and the current consumed while supplying the power during the second set time in the third set time cycle shorter than the first set time cycle is between the set lower and upper limit values.

The first logic may include determining that the moisture formed on the first sensor may have evaporated, when a run time of the engine after a startup of the engine exceeds a set value.

The second logic may include after determining that the moisture formed on the first sensor may have evaporated, checking the evaporation of the moisture formed on the second sensor with an accumulation of time after a startup of the engine The first sensor, second sensor, and other sensors are either, lambda sensors which respond to oxygen concentration, nitrogen oxide sensors which react with nitrogen oxides, PM sensors which react with particulate matters, or temperature sensors which responsive to temperature of exhaust gases.

The second logic may include supplying power to a second sensor heater for heating the second sensor during a second set time in a first set time cycle, determining whether a current consumed by the second sensor is between set lower and upper limit values, supplying power to the second sensor heater of the second sensor during the second set time in a third set time cycle shorter than the first set time cycle, determining again whether the current consumed by the second sensor is between the set lower and upper limit values, and determining whether the moisture formed on the second sensor may have evaporated, when the current consumed while supplying the power during the second set time in the first set time cycle is between the set lower and upper limits, and the current consumed while supplying the power during the second set time in the third set time cycle shorter than the first set time cycle is between the set lower and upper limit values.

The first sensor is disposed adjacent to the engine.

As described above in detail, the control method of a sensor disposed in an exhaust system according to the exemplary embodiment of the present invention makes it easy to check the evaporation of moisture formed on sensors installed in an exhaust line by temperature sensors installed in the exhaust line, the RPM of the engine, a method of periodically supplying power to sensor heaters, the cumulative amount of fuel injection, the run time of the engine, and so on.

Accordingly, if it is determined that all the moisture has evaporated, power is applied to the sensor heaters, thereby improving the durability of the sensors and preventing malfunctioning.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1A:
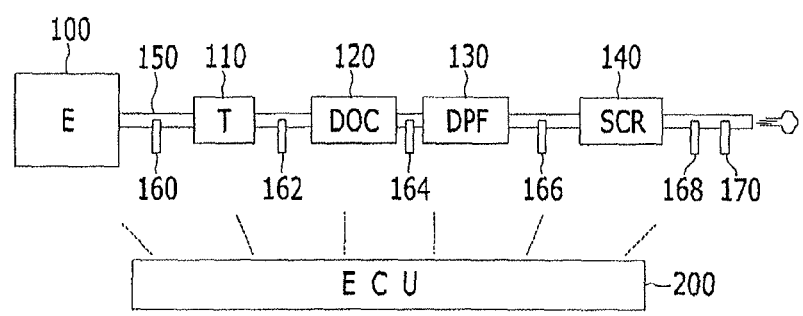
FIGS. 1A, 1B, and 1C are schematic block diagrams showing an engine and an exhaust system according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention (s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

An exemplary embodiment of the present invention will hereinafter be described in detail with reference to the accompanying drawings.

Figure 1B:
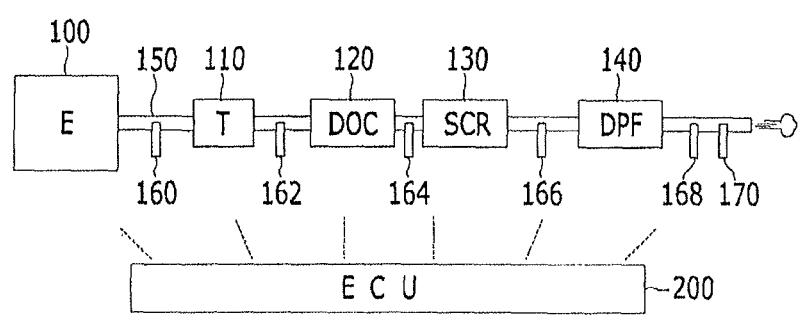
Figure 1C:
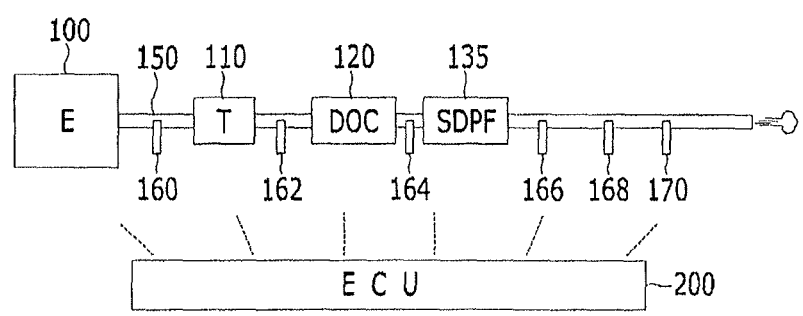

FIGS. 1A, 1B, and 1C are schematic block diagrams showing an engine and an exhaust system according to an exemplary embodiment of the present invention.

Referring to FIG. 1A, the exhaust system includes an engine 100, an exhaust line 150, a turbocharger 110, a diesel oxidation catalyst 120, a diesel particulate filter 130, a selective catalytic reduction device 140, a first sensor 160, a second sensor 162, a third sensor 164, a fourth sensor 166, a fifth sensor 168, a sixth sensor 170, and a controller 200.

The turbocharger 110, the diesel oxidation catalyst 120, the diesel particulate filter 130, and the selective catalytic reduction device 140 are sequentially disposed in the exhaust line 150.

The turbocharger 110 is powered by the energy flow in exhaust gases to compress intake air flowing through an intake line and supply the compressed intake air to a combustion chamber, the diesel oxidation catalyst 120 reduces harmful gases in the exhaust gases, and the diesel particulate filter 130 filters particulate matters in the exhaust gases. The selective catalytic reduction device 140 stores and removes the nitrogen oxides contained in the exhaust gases.

The first sensor 160 is installed in front of the turbocharger 110, the second sensor 162 is disposed between the turbocharger 110 and the diesel oxidation catalyst 120, the third sensor 164 is disposed between the diesel oxidation catalyst 120 and the diesel particulate filter 130, the fourth sensor 166 is disposed between the diesel particulate filter 130 and the selective catalytic reduction device 140, and the fifth sensor 168 and the sixth sensor 170 are disposed at the rear of the selective catalytic reduction device 140.

The first sensor 160, the second sensor 162, the third sensor 164, the fourth sensor 166, the fifth sensor 168, and the sixth sensor 170 are for detecting physicochemical characteristics of and particulate matters in the exhaust gases passing through the exhaust line 150. They may be either Lambda sensors, nitrogen oxide sensors, PM sensors, or temperature sensors.

The lambda sensors are sensors which respond to oxygen concentration, the nitrogen oxide sensors are sensors which react with nitrogen oxides, the PM sensors are sensors which react with particulate matters, and the temperature sensors are temperature-responsive sensors.

In the exemplary embodiment of the present invention, the first sensor 160, the second sensor 162, the third sensor 164, the fourth sensor 166, the fifth sensor 168, and the sixth sensor 170 are each equipped with a sensor heater and these sensor heaters heat the sensors to keep the sensors at a set temperature (around 800° C.).

Meanwhile, when the engine 100 stops working, the exhaust line 150 is cooled to produce condensed water from the exhaust gases, and this condensed water is formed in the form of moisture on each sensor. When the engine 100 is started and the temperature of the exhaust gases rises, the moisture formed on each sensor evaporates.

However, when power is applied to the sensor heaters that heat the sensors, with moisture present on each sensor, this may deteriorate the durability of the sensors and cause the sensors to operate abnormally.

Accordingly, the exemplary embodiment of the present invention can improve the durability of the sensors and prevent them from operating abnormally, by heating the sensors by the sensor heaters after the moisture formed on each sensor evaporates.

The controller 200 detects the RPM of the engine 100 from the engine 100, detects the temperature of the exhaust gases passing through the exhaust line 150 from the first, second, third, fourth, fifth, and sixth sensors 160, 162, 164, 166, 168, and 170, detects the amount of fuel injection from an injector, detects the time elapsed after starting up the engine 100, and controls the power supply to the sensor heaters of sensors required to be heated, among the first, second, third, fourth, fifth, and sixth sensors 160, 162, 164, 166, 168, and 170.

Moreover, the controller 200 performs the logic of checking whether moisture formed on the first sensor 160 has evaporated and the logic of checking whether moisture formed on the second sensor 162 has evaporated.

In addition, the controller 200 performs the logic of sequentially detecting whether moisture formed on the third, fourth, fifth, and sixth sensors 164, 166, 168, and 170 has evaporated. A method of performing these logics will be described in detail with reference to FIGS. 2A, 2B, 2C, and 2D.

Referring to FIG. 1B, in comparison with FIG. 1A, the positions of the selective catalytic reduction device 140 and diesel particulate filter 130 are switched. Referring to FIG. 1C, a single SDPF 135 replaces the diesel particulate filter 130 and the selective catalytic reduction device 140. The fourth, fifth, and sixth sensors 166, 168, and 170 are sequentially disposed at the rear of the SDPF 135.

FIGS. 2A, 2B, 2C, and 2D are flowcharts showing a method of checking the evaporation of a first sensor of an exhaust line according to an exemplary embodiment of the present invention.

Figure 2A:
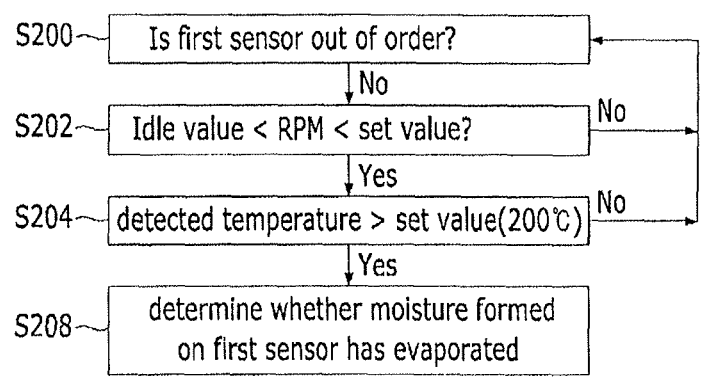
FIGS. 2A, 2B, 2C, and 2D are flowcharts showing a method of checking the evaporation of moisture formed on a first sensor of an exhaust line according to an exemplary embodiment of the present invention.

Referring to FIG. 2A, in S200, it is determined if the first sensor 160 installed in front of the turbocharger 110 is out of order or not. In S202, it is determined whether the RPM of the engine 100 is between a preset idle value and a set value.

In S204, it is determined whether the temperature of exhaust gases detected by the first sensor 160, a temperature sensor for detecting the temperature of exhaust gases, is higher than a set value (200° C.) and whether this temperature is maintained for 1 hour.

In S208, it is determined whether moisture on the first sensor 160 has evaporated. Although, in an exemplary embodiment of the present invention, the first sensor 160 is a temperature sensor, it may be a different type of sensor, as described above.

That is, if the first sensor 160 is not out of order, the RPM of the engine 100 is within a set value range, and the temperature of exhaust gases is higher than a set value, the controller 200 determines that all the moisture formed on the first sensor 160 has evaporated.

Figure 2B:
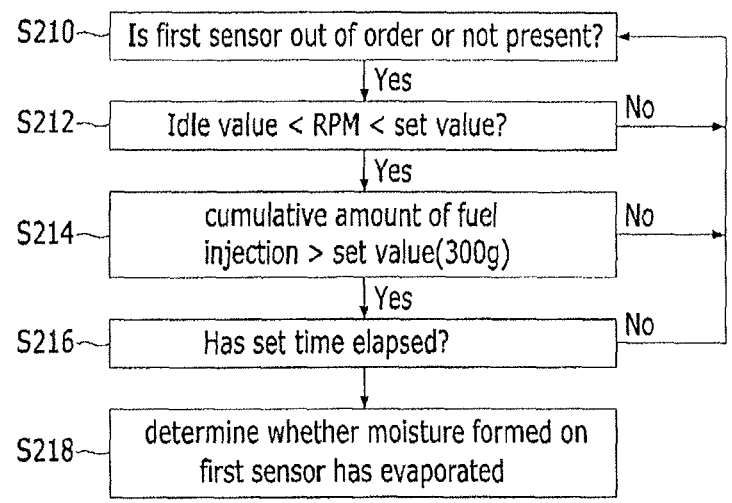

Referring to FIG. 2B, in S210, it is determined if the first sensor 160 is out of order or not installed. In S212, it is determined whether the RPM of the engine 100 is between a preset idle value and a set value.

In S214, the controller 200 determines whether the cumulative amount of fuel injection from an injector is greater than a set value (around 300 g). In S216, it is determined if a set time has elapsed after the engine 100 is started.

In S218, it is determined whether moisture formed on the first sensor 160 has evaporated.

That is, if the first sensor 160 is not out of order, the RPM of the engine 100 is within a set value range, and the cumulative amount of fuel injection is higher than a set value, and the engine 100 has worked for a set time, the controller 200 determines that all the moisture formed on the first sensor 160 has evaporated.

Figure 2C:
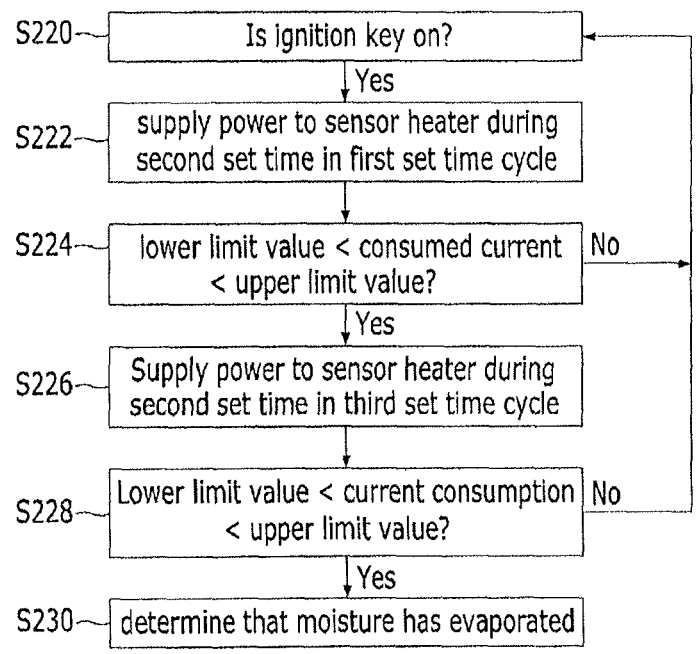

FIG. 2C illustrates a method of determining whether moisture formed on any one of the first, second, third, fourth, fifth, and sixth sensors 160, 162, 164, 166, 168, and 170 has evaporated.

For convenience of explanation, a method of determining whether moisture formed on the first sensor 160 has evaporated will be described with reference to FIG. 2C.

Referring to FIG. 2C, in S220, it is determined whether an ignition key for starting the engine 100 is at the on position.

In S222, power is supplied to a first sensor heater for heating the first sensor 160 during a second set time in a first set time cycle. In the exemplary embodiment of the present invention, the first set time cycle may be 30 seconds, and the second set time may be 0.3 seconds.

In S224, it is determined whether the value of current consumed by the first sensor 160 is between preset lower and upper limit values. In S226, power is supplied to the first sensor heater during the second set time in a third set time cycle. In the exemplary embodiment of the present invention, the third set time cycle may be 3 seconds, and the second set time may be 0.3 seconds.

The third set time cycle is shorter than the first set time cycle, and the second set time is set such that the first sensor 160 is kept from malfunctioning or going out of order even when power is supplied to the sensor heater of the first sensor 160 with moisture formed on it.

In S228, it is determined whether the value of current consumed by the first sensor 160 is between preset lower and upper limit values. In S230, it is determined whether the moisture formed on the first sensor 160 has evaporated.

That is, if the ignition key is on, power is applied to a first load by the first sensor heater in S222 and the power consumption is within a set range, and power is applied to a second load, higher than the first load, by the first sensor heater in S226 and the power consumption is within the set range, it is determined that all the moisture formed on the first sensor 160 has evaporated in S230.

Referring to FIG. 2C, if the current consumed by the first sensor heater is within the preset lower and upper limit values, this means that the moisture formed on the first sensor 160 or its corresponding position has evaporated. That is, if the current consumed by the first sensor heater exceeds the preset upper limit value, this means that not all the moisture has evaporated.

Figure 2D:
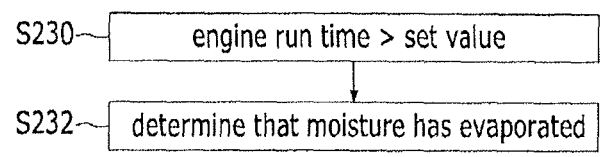

Referring to FIG. 2D, if the run time of the engine 100 exceeds a preset value (around 20 minutes) in S230, it is determined that all the moisture formed on the first sensor 160 has evaporated in S232.

Figure 3:
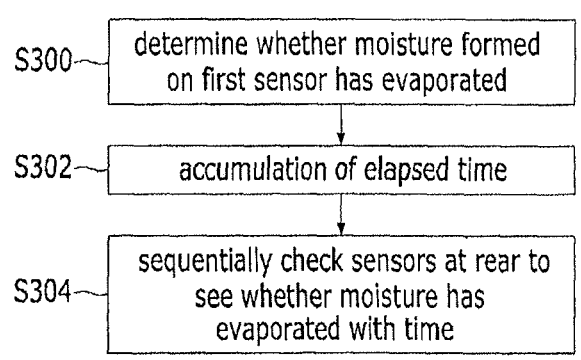
FIG. 3 is a flowchart showing a method of sequentially checking the evaporation of moisture formed in an exhaust line according to an exemplary embodiment of the present invention.

FIG. 3 is a flowchart showing a method of sequentially checking the evaporation of moisture formed in an exhaust line according to an exemplary embodiment of the present invention.

In S300, it is determined whether moisture formed on a predetermined first sensor 160 has evaporated. The elapsed time is accumulated in S302, and the second, third, fourth, fifth, and sixth sensors 162, 164, 166, 168, and 170 disposed at the rear of the first sensor 160 are sequentially checked to see whether the moisture formed on them has evaporated with time in S304.

In the exemplary embodiment of the present invention, the evaporation of moisture formed on sensors with time is confirmed through preset experimental data or stored map data.

The evaporation of moisture formed on the first sensor 160 is confirmed by the method of FIG. 2A, FIG. 2B, FIG. 2C, or FIG. 2D, and the evaporation of the second, third, fourth, fifth, and sixth sensors 162, 164, 166, 168, and 170 is confirmed by the method of FIG. 3.

Figure 4:
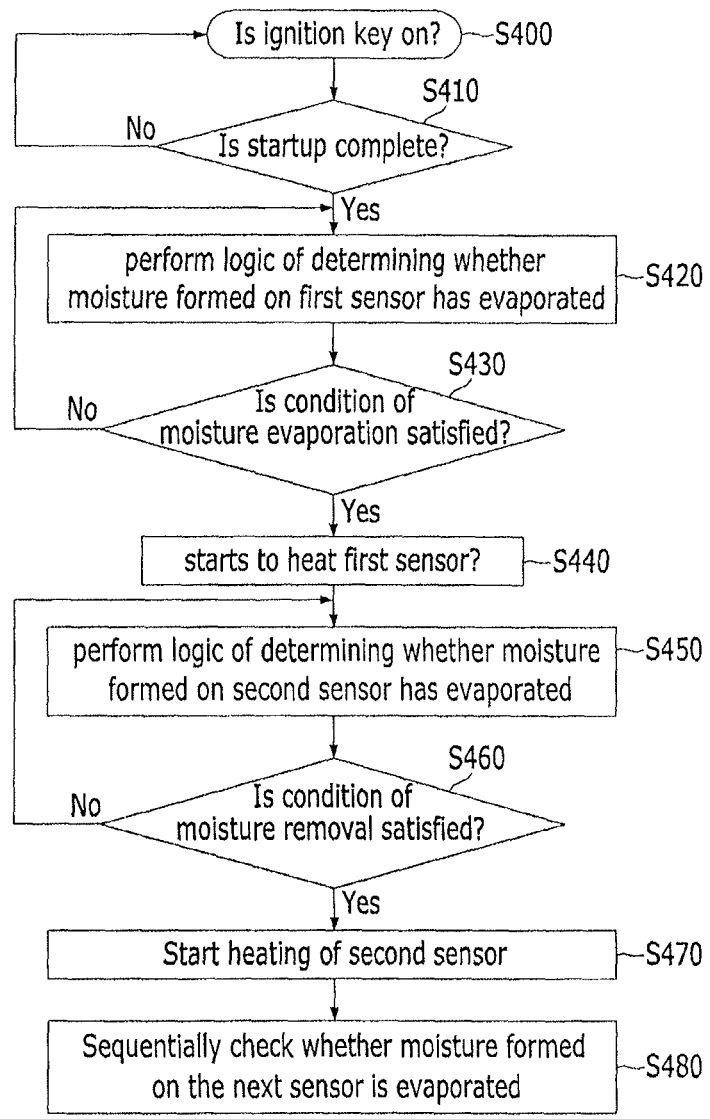
FIG. 4 is a flowchart showing a control method of sensors disposed in an exhaust system according to an exemplary embodiment of the present invention.

FIG. 4 is a flowchart showing a control method of sensors disposed in an exhaust system according to an exemplary embodiment of the present invention.

Referring to FIG. 4, it is checked whether the ignition key is on in S400, and it is determined whether the engine 100 is started in S410.

In S420, a first logic is performed to determine whether moisture formed on the first sensor 160, closest to the engine 100, in the exhaust line 150 has evaporated.

In S430, it is determined by the first logic whether the condition of moisture removal is satisfied. If this condition is not satisfied, S420 is performed. If this condition is satisfied, S440 is performed. In S440, the first sensor 160 is heated through a first sensor heater.

Next, a second logic is performed to determine whether moisture formed on the second sensor 162 disposed at the rear of the first sensor 160 has evaporated in S450, and it is determined by the second logic whether the condition of moisture removal is satisfied in S460.

If this condition is not satisfied, S450 is performed. If this condition is satisfied, S470 is performed. In S470, the second sensor 162 is heated through a second sensor heater.

Next, the sensors at the rear of the second sensor 162 are sequentially checked whether moisture formed on them has evaporated in S480.

In FIG. 4, the first logic may include one of the methods explained with reference to FIG. 2A, FIG. 2B, FIG. 2C, and FIG. 2D, and the second logic may include one of the methods explained with reference to FIG. 2B, FIG. 2C, FIG. 2D, and FIG. 3.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A control method of a sensor disposed in an exhaust system, the control method comprising:
    starting an engine;
    performing a first logic of checking whether moisture formed on a first sensor detecting one of characteristics of exhaust gases emitted from the engine;
    heating the first sensor when it is determined by the first logic that the moisture formed on the first sensor has evaporated; and
    performing a second logic of checking whether moisture formed on a second sensor disposed at a rear of the first sensor and detecting one of the characteristics of the exhaust gases,
    wherein the first logic comprises:
        supplying power to a first sensor heater for heating the first sensor during a second set time in a first set time cycle;
        determining whether a current consumed by the first sensor is between set lower and upper limit values;
        supplying power to the first sensor heater of the first sensor during the second set time in a third set time cycle shorter than the first set time cycle;
        determining again whether the current consumed by the first sensor is between the set lower and upper limit values; and
        determining whether the moisture formed on the first sensor has evaporated, when the current consumed while supplying the power during the second set time in the first set time cycle is between the set lower and upper limits, and the current consumed while supplying the power during the second set time in the third set time cycle shorter than the first set time cycle is between the set lower and upper limit values.

2. The control method of claim 1, comprising:
    heating the second sensor, when it is determined by the second logic that the moisture formed on the second sensor has evaporated; and
    sequentially checking evaporation of moisture formed on other sensors disposed at a rear of the second sensor and each detecting one of the characteristics of the exhaust gases.

3. The control method of claim 1, wherein the first logic comprises:
    checking whether the first sensor detecting a temperature of the exhaust gases is out of order;
    determining whether an RPM of the exhaust gases is within a set value range;
    determining whether the temperature of the exhaust gases detected by the first sensor is higher than a set value; and
    determining that the moisture formed on the first sensor has evaporated, when the first sensor is not out of order, the RPM of the engine is within the set value range, and the temperature of the exhaust gases is higher than the set value.

4. The control method of claim 3, further including: determining whether the temperature of the exhaust gases detected by the first sensor is maintained for a predetermined time period.

5. The control method of claim 1, wherein the first logic comprises:
    checking whether the first sensor is out of order or not present;
    determining whether an RPM of the engine is within a set value range;
    determining whether a cumulative amount of fuel injection after a startup of the engine is greater than a set value;
    determining whether a set time has elapsed after the startup of the engine; and
    determining that the moisture formed on the first sensor has evaporated, when the first sensor is out of order or not present, the RPM of the engine is within the set value range, the cumulative amount of fuel injection is greater than the set value, and the set time has elapsed.

6. The control method of claim 1, wherein the first logic comprises:
  determining that the moisture formed on the first sensor has evaporated, when a run time of the engine after a startup of the engine exceeds a set value.

7. The control method of claim 1, wherein the second logic comprises:
  after determining that the moisture formed on the first sensor has evaporated, checking the evaporation of the moisture formed on the second sensor with an accumulation of time after a startup of the engine.

8. The control method of claim 2, wherein the first sensor, second sensor, and other sensors are either, lambda sensors which respond to oxygen concentration, nitrogen oxide sensors which react with nitrogen oxides, PM sensors which react with particulate matters, or temperature sensors which responsive to temperature of exhaust gases.

9. The control method of claim 1, wherein the second logic comprises:
  supplying power to a second sensor heater for heating the second sensor during a second set time in a first set time cycle;
  determining whether a current consumed by the second sensor is between set lower and upper limit values;
  supplying power to the second sensor heater of the second sensor during the second set time in a third set time cycle shorter than the first set time cycle;
  determining again whether the current consumed by the second sensor is between the set lower and upper limit values; and
  determining whether the moisture formed on the second sensor has evaporated, when the current consumed while supplying the power during the second set time in the first set time cycle is between the set lower and upper limits, and the current consumed while supplying the power during the second set time in the third set time cycle shorter than the first set time cycle is between the set lower and upper limit values.

10. The control method of claim 1, wherein the first sensor is disposed adjacent to the engine.

11. A control method of a sensor disposed in an exhaust system, the control method comprising:
  starting an engine;
  performing a first logic of checking whether moisture formed on a first sensor detecting one of characteristics of exhaust gases emitted from the engine;
  heating the first sensor when it is determined by the first logic that the moisture formed on the first sensor has evaporated; and
  performing a second logic of checking whether moisture formed on a second sensor disposed at a rear of the first sensor and detecting one of the characteristics of the exhaust gases,
  wherein the second logic comprises:
    supplying power to a second sensor heater for heating the second sensor during a second set time in a first set time cycle;
    determining whether a current consumed by the second sensor is between set lower and upper limit values;
    supplying power to the second sensor heater of the second sensor during the second set time in a third set time cycle shorter than the first set time cycle;
    determining again whether the current consumed by the second sensor is between the set lower and upper limit values; and
    determining whether the moisture formed on the second sensor has evaporated, when the current consumed while supplying the power during the second set time in the first set time cycle is between the set lower and upper limits, and the current consumed while supplying the power during the second set time in the third set time cycle shorter than the first set time cycle is between the set lower and upper limit values.

* * * * *